United States Patent
Smith et al.

(10) Patent No.: US 10,512,443 B2
(45) Date of Patent: Dec. 24, 2019

(54) SYSTEMS AND METHODS FOR VIBRATION DETECTION

(71) Applicant: General Electric Company, Schenectady, NY (US)

(72) Inventors: Chad Allan Smith, Franklin, WI (US); Mark Edmund Reznicek, Sussex, WI (US); Ariel Friedlander, Mequon, WI (US)

(73) Assignee: General Electric Company, Schenectady, NY (US)

( * ) Notice: Subject to any disclaimer, the term of this patent is extended or adjusted under 35 U.S.C. 154(b) by 109 days.

(21) Appl. No.: 15/818,585

(22) Filed: Nov. 20, 2017

(65) Prior Publication Data

US 2019/0150878 A1 May 23, 2019

(51) Int. Cl.
*A61B 6/00* (2006.01)
*A61B 6/03* (2006.01)

(52) U.S. Cl.
CPC .............. *A61B 6/586* (2013.01); *A61B 6/032* (2013.01); *A61B 6/035* (2013.01); *A61B 6/5205* (2013.01); *A61B 6/527* (2013.01); *A61B 6/4435* (2013.01)

(58) Field of Classification Search
None
See application file for complete search history.

(56) References Cited

U.S. PATENT DOCUMENTS

| | | | |
|---|---|---|---|
| 7,023,952 B2 | 4/2006 | Brunnett | |
| 2005/0013403 A1* | 1/2005 | Reznicek | A61B 6/035 378/15 |
| 2005/0281391 A1 | 12/2005 | Luo et al. | |
| 2008/0025460 A1 | 1/2008 | Li | |
| 2017/0188988 A1 | 7/2017 | Aasen | |

* cited by examiner

*Primary Examiner* — Hoon K Song
(74) *Attorney, Agent, or Firm* — McCoy Russell LLP

(57) ABSTRACT

Methods and systems are provided for measuring vibrations in an imaging system. In one embodiment, a method for a computed tomography (CT) system includes measuring a vibration level of a rotatable gantry of the CT system with a balance sensor coupled to a stationary housing of the CT system and outputting a notification indicating potential image artifacts based on the vibration level exceeding a vibration threshold.

19 Claims, 5 Drawing Sheets

SYSTEMS AND METHODS FOR VIBRATION DETECTION

FIELD

Embodiments of the subject matter disclosed herein relate to medical imaging, and more particularly, to detecting vibration in a computed tomography scanner.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures). CT scanners may include a rotatable gantry on which a radiation source and detectors are mounted. The vibration of the gantry as it rotates directly translates to degradation in image quality, as gantry vibration can distort images and create streaks/artifacts in the patient data.

BRIEF DESCRIPTION

In one embodiment, a method for a computed tomography (CT) system includes measuring a vibration level of a rotatable gantry of the CT system with a balance sensor coupled to a stationary housing of the CT system and outputting a notification indicating potential image artifacts based on the vibration level exceeding a vibration threshold. In this way, vibrations of the CT system that may produce image artifacts or other image quality issues may be detected with an on-board balance sensor.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of measuring vibration of a computed tomography (CT) scanner. Traditionally, CT scanners may have sensors on board the CT scanner that are used to measure gantry imbalance (imbalance occurs once per rotation), but are not used to measure full gantry vibration which can have different harmonics occurring at more than once per rotation. Typically, to measure vibration, expensive external laboratory-type commercial analyzers may be used when the CT scanner is being built or refurbished at the factory. Then, because external laboratory-type commercial vibration analyzers are not usually suitable for field service usage due to their high cost and required training, gantry imbalance measurements may relied upon for detecting gantry rotation issues once the CT scanner is installed in a location. However, many factors may effect gantry vibration after installation in addition to imbalance, including floor stiffness and gantry anchoring. Thus, by relying only the imbalance measurement after installation, higher order vibrations (e.g., vibrations that occur two or more times per rotation of the gantry) may go undetected. As mentioned above, vibrations may result in poor image quality.

Thus, according to embodiments disclosed herein, the balance sensors on the CT scanner may be used to measure vibrations at nearly any suitable time during the lifetime of the CT scanner. Herein, the motion/vibration amplitude values for each rotation speed of the gantry are determined by sampling data from the on-board balance sensors (while CT scanner gantry is rotating at constant speed), deconvolving the digitized sensing signals with an inverse sensing subsystem transfer function in the frequency domain, and then extracting target harmonic frequency responses that have been determined to be the most dominant frequencies, such as the first six harmonic frequency responses. The target harmonic frequency responses (e.g., peak to peak amplitudes) may then be compared to respective thresholds to determine the level of vibration of the gantry. If the gantry is vibrating at a detectable/high level, an operator may be notified that the CT scanner may need be serviced. Further, by analyzing the different harmonic frequency responses individually, the cause of the vibration may be identified or predicted, expediting service of the CT scanner.

Though a CT system is described by way of example, it should be understood that the present techniques may also be useful when applied to other rotatable bodies, such as centrifuges, wind turbines, and so forth. The present discussion of a CT imaging modality is provided as an example of one suitable rotatable body.

Figure 1:
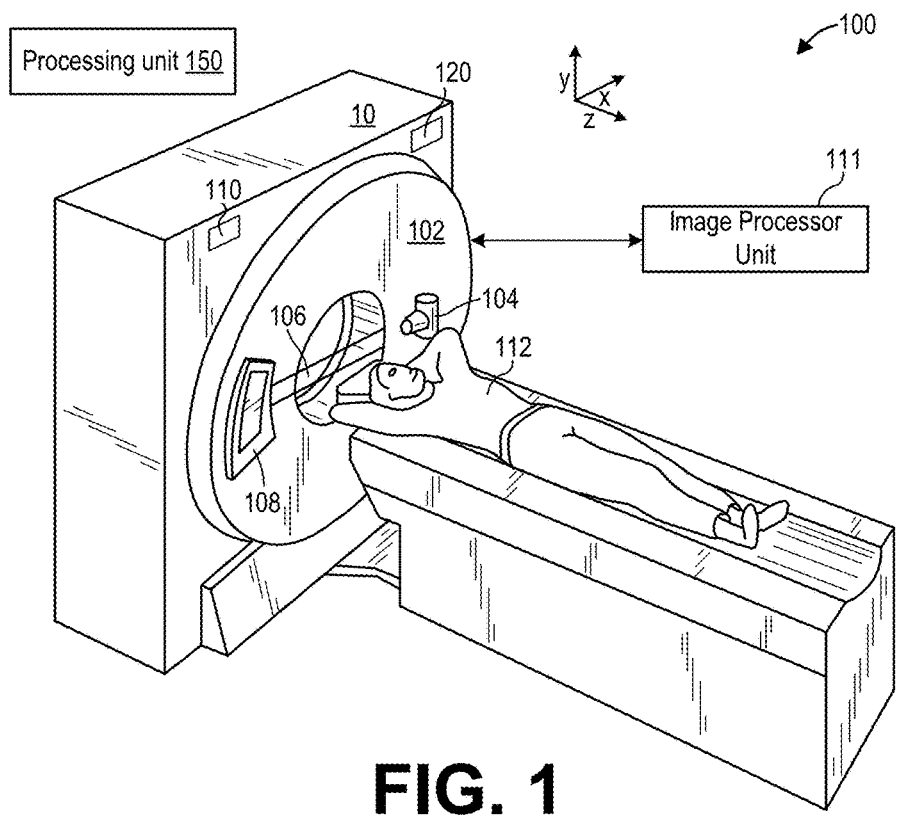
FIG. 1 shows a pictorial view of an example imaging system.

FIG. 1 illustrates an exemplary CT system 100. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a stationary housing 10 that houses a gantry 102, which in turn, may further include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources may be employed to project a plurality of x-rays 106 for acquiring projection data corresponding to the subject 112 at different energy levels.

In certain embodiments, the CT system 100 further includes an image processor unit 111 configured to reconstruct images of a target volume of the subject 112 using an iterative or analytic image reconstruction method. For example, the image processor unit 111 may use an analytic image reconstruction approach such as filtered backprojection (FBP) to reconstruct images of a target volume of the patient. As another example, the image processor unit 111 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two-dimensional slice taken through the object. One method for reconstructing an image from a set of projection data is referred to in the art as the filtered backprojection (FBP) technique. Transmission and emission tomography reconstruction techniques also include statistical iterative methods such as maximum likelihood expectation maximization (MLEM) and ordered-subsets expectation reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate (or are configured to generate) at least one viewable image.

The CT system 100 further includes a first balance sensor 110 and a processing unit 150. The first balance sensor 110 (and/or other balance sensors discussed herein) is configured to provide vibration information at a first frequency, and vibration information at a second frequency, with the second frequency higher than the first frequency. It may be noted that the first frequency and/or second frequency may include a range of frequencies. The first frequency may include a range that is adjacent to a range of the second frequency (e.g., the first frequency including a range of 0-1 Hertz and the second frequency including a range of 1-5 Hertz), or the first frequency may include a range that is spaced a distance or gap from a range of the second frequency (e.g., the first frequency including a range of 0-0.5 Hertz and the second frequency including a range of 1-5 Hertz).

An inclinometer is an example of balance sensor 110. Other balance sensors may be employed additionally or alternatively in various embodiments. The first balance sensor 110 (and/or other balance sensors discussed herein) in various embodiments may be a Micro-Electro-Mechanical System (MEMS) based accelerometer that includes a mechanical configuration, such as inclusion of a dampening gas, configured to limit the frequency output of the MEMS based accelerometer. An example of a MEMS based inclinometer is the Murata SCA103T differential inclinometer series. The first balance sensor 110 (and/or other balance sensors discussed herein) may include a cantilevered mass and spring, with the mass disposed between plates and causing a measurable change in capacitance between the two plates as the mass vibrates. The mass and spring of the first balance sensor 110 may be vibrated below a resonant frequency in various embodiments. The first balance sensor 110 (and/or other balance sensors discussed herein) may be mounted to the stationary housing 10 as far as practicable from a mounting mechanism or feet of the stationary housing (or otherwise positioned on a portion of the stationary housing 10 that will vibrate the most when subject to a vibration from the gantry 102), for example, to improve the signal to noise ratio of an output generated responsive to the vibration.

In various embodiments, the first balance sensor 110 may have one or more axes of sensitivity. For example, the first balance sensor 110 may have one axis of sensitivity that corresponds to a static vibration (or corresponding state of balance) and a second axis of sensitivity that corresponds to a dynamic vibration (or corresponding state of balance). The first and second axes may be perpendicular to each other. For example, the first balance sensor 110 may have a first axis of sensitivity that corresponds to a trans-axial plane of the subject 112 (for example, aligned with the x axis of the coordinate system illustrated in FIG. 1) and a second axis of sensitivity that corresponds to the long axis of the subject 112 (e.g., aligned with the z axis of the coordinate system and where the sagittal and coronal planes intersect). Accordingly, the depicted first balance sensor 110 may be understood as having plural axes of sensitivity. Additionally or alternatively, as discussed herein, the first balance sensor 110 may have only one axis of sensitivity and/or one or more additional balance sensors may be utilized.

The depicted processing unit 150 is operably coupled to the first balance sensor 110, and is configured to acquire the vibration information from the first balance sensor 110. Also, the processing unit 150 is configured to determine a state of balance of the gantry 102 using the vibration information, but not the inclination information. For example, the processing unit 150 may receive the inclination information, but discard or disregard the inclination information. As another example, the CT system 100 may be configured to prevent all or a portion of the inclination information from being provided to the processing unit 150. For example, a filter or filters may be interposed between the processing unit 150 and the first balance sensor 110 and utilized to remove the inclination information from a signal provided from the first balance sensor 110 to the processing unit 150. The processing unit 150 may determine the state of balance based on or using a predetermined relationship or correlation between information received via one or more output signals from one or more inclinometers to the state of balance. The predetermined relationship may be stored and/or expressed in a formula, look-up table, or the like. Accordingly, based on vibration information received from one or more balance sensors (e.g., based on a portion of the output signal(s) from one or more balance sensors corresponding to vibration instead of inclination), the processing unit 150 may determine whether the gantry 102 is in an acceptable state of balance, how the gantry 102 is deviating from an acceptable state of balance (if not in balance), and/or how to mitigate or correct an imbalance (e.g., by specifying an amount and location of masses to be mounted to gantry 102). Further, as will be explained in more detail below, the signal from the balance sensor(s) may be used to determine gantry vibration at higher orders than imbalance.

For example, during a manufacture, inspection, or installation stage of the gantry 102 (e.g., with the gantry 102 coupled to the stationary housing 10) or comparable or equivalent rotating member, known imbalances may be applied to the rotating member, such as by adding mass in a predetermined amount at one or more predetermined locations of the rotating member. Then, with one or more balance sensors mounted to the stationary housing, the outputs from the one or more balance sensors generated responsive to a known rotation (e.g., at a given rotational speed) of the rotating member with the known imbalances applied may be recorded. By using a series of different amounts and/or locations of applied imbalances, a relationship between the balance sensor output and particular imbalances may be defined. A state of balance as used herein may refer to whether or not a rotating member is perfectly balanced (or within a tolerable margin of perfect balance). In some embodiments, the state of balance may also include an identification of where or how much the rotating member deviates from perfect balance and/or a configuration (e.g., amount and location of placement) of corrective masses to be applied to the rotating member to put the rotating member in a state of perfect balance (or within a tolerable margin).

In various embodiments, the processing unit 150 includes processing circuitry configured to perform one or more tasks, functions, or steps discussed herein. It may be noted that "processing unit" as used herein is not intended to necessarily be limited to a single processor or computer. For example, the processing unit 150 may include multiple processors and/or computers, which may be integrated in a common housing or unit, or which may be distributed among various units or housings. All or a portion of the processing unit 150 may be mounted on the stationary housing 10 in various embodiments, while in other embodiments the processing unit 150 may be separately housed or mounted from the stationary housing 10. It may be noted that operations performed by the processing unit 150 (e.g., operations corresponding to process flows or methods discussed herein, or aspects thereof) may be sufficiently complex that the operations may not be performed by a human being within a reasonable time period. For example, the analysis of signals from the balance sensors and/or determination of a state of balance may not be performed by a human being within a reasonable time period. Processing unit 150 may include a memory. The memory may include one or more computer readable storage media. The memory for example, may store acquired and/or processed signals received from one or more inclinometers or other balance sensors, correlations or relationships between signals received from inclinometers and states of balance of the gantry, or the like. Further, the methods and routines discussed herein (or aspects thereof) may represent one or more sets of instructions that are stored in the memory for direction of operations of the CT system 100.

It may be noted that, in some embodiments, more than one balance sensor may be employed. For example, in the embodiment depicted in FIG. 1, in addition to the first balance sensor 110, the CT system 100 includes a second balance sensor 120. In various embodiments, the second balance sensor 120 may have an axis of sensitivity that differs from an axis of sensitivity of the first balance sensor 110. The second balance sensor 120 may be generally similar to the first balance sensor 110 in various respects. In the illustrated embodiment, the second balance sensor 120 is configured to provide second vibration information at a third frequency and at a fourth frequency. The fourth frequency is higher than the third frequency. The fourth frequency of the second balance sensor 120 may be the same as the second frequency of the first balance sensor 110, and the third frequency of the second balance sensor 120 may be the same as the first frequency of the first balance sensor 110. The depicted second balance sensor 120 has an axis of sensitivity that may be aligned with the long axis of the subject 112, for example. When the second balance sensor 120 is used in conjunction with the first balance sensor 110 in various embodiments, the second balance sensor 120 may provide information measured with respect to the axis of sensitivity aligned with the long axis while the first balance sensor 110 is used to obtain information along the axis of sensitivity aligned with the trans-axial plane. Thus, the first balance sensor 110 and the second balance sensor 120 may be used to provide information for different axes of sensitivity (e.g., axes that are perpendicular to each other). It may be noted that in various embodiments, plural first balance sensors 110 (or balance sensors having a common first axis of sensitivity) may be utilized. Further, plural first balance sensors 110 (or balance sensors having a common first axis of sensitivity) may be utilized in conjunction with plural second balance sensors 120 (or balance sensors having a common second axis of sensitivity that is different than the common first axis of sensitivity of the plural first balance sensors 110).

Figure 2:
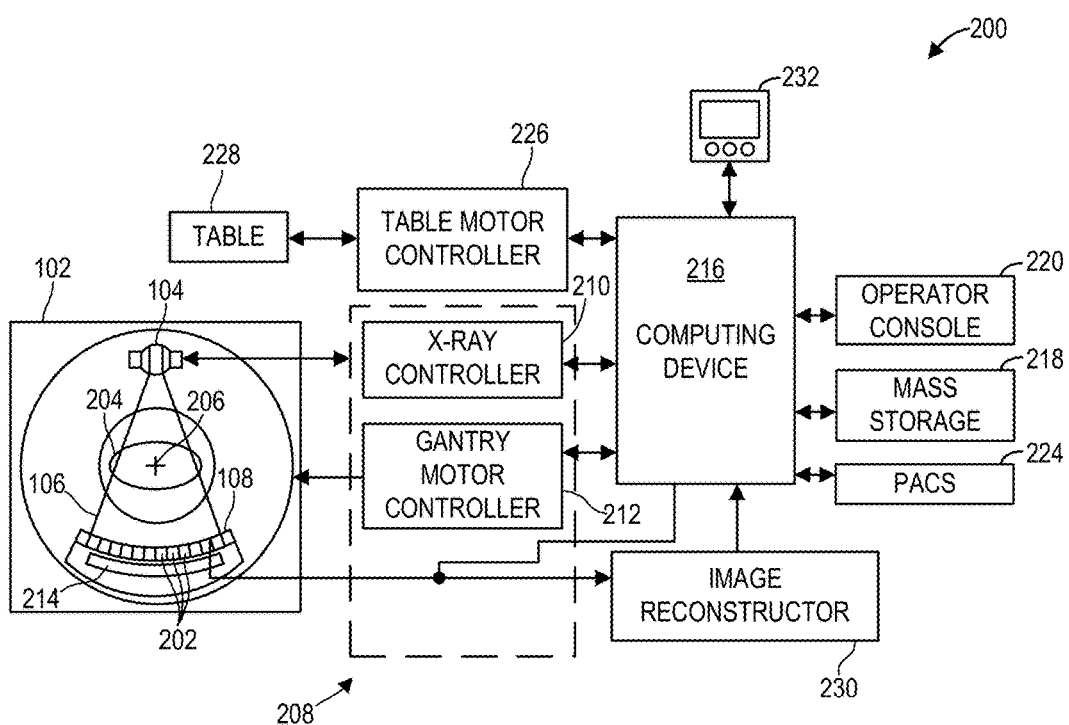
FIG. 2 shows a block schematic diagram of an example imaging system.

FIG. 2 illustrates an exemplary imaging system 200 similar to the CT system 100 of FIG. 1. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray radiation source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device such as mass storage 218. The mass storage 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) and/or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more of the functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device or mass storage 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. For example, image reconstructor 230 may include such executable instructions in non-transitory memory, and may apply the instructions to reconstruct an image from scanning data. Computing device 216 may include instructions in non-transitory memory, and may apply the methods described herein, at least in part, to measure gantry imbalance and/or vibration. In yet another embodiment, the methods and processes described herein may be distributed across computing device 216 and other computing devices, such as a remote computing device.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing. Further, as will be described in more detail below, information regarding imbalance and/or vibration of the gantry of the CT system may be displayed via display 232.

Figure 3:
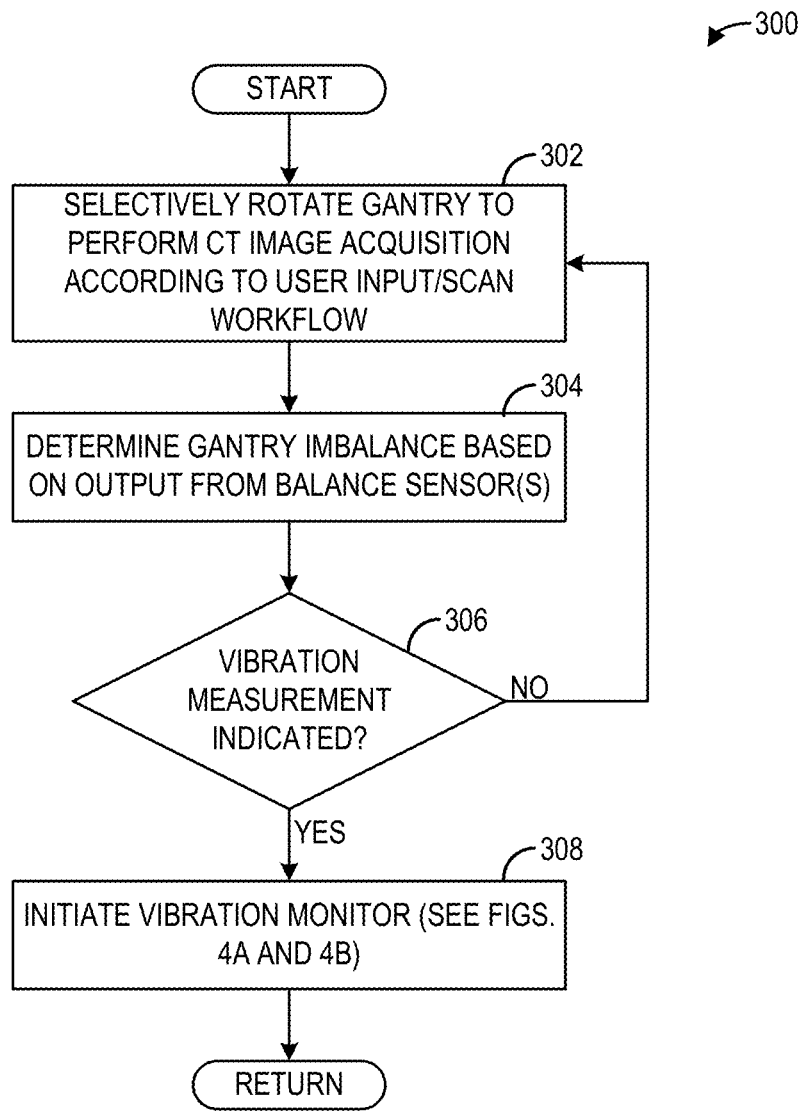
FIG. 3 is a flow chart illustrating a method for operating an imaging system.

Turning to FIG. 3, a method 300 for operating a CT system is shown. Method 300 is described with regard to the systems and components depicted in FIGS. 1 and 2, though it should be appreciated that the method may be implemented with other systems and/or components without departing from the scope of the present disclosure. Method 300 may be implemented as executable instructions in non-transitory memory of a computing device, such as computing device 216.

At 302, method 300 includes selectively rotating a gantry (such as gantry 102 of FIG. 1) to perform CT image acquisition according to user input and/or a workflow protocol. For example, when a subject to be imaged is positioned within the imaging space of the imaging system (e.g., within the gantry) and an operator indicates a CT scan is to be performed (e.g., via input to a user input device of the imaging system), the gantry may be rotated to perform the scan. While the gantry is rotated, the radiation source coupled to the gantry (e.g., source 104) may be activated to transmit radiation to the subject and the radiation detector (e.g., detector array 108) may receive radiation that is not attenuated by the subject. The signals received by the radiation detector (which may be referred as the projection data) may be sent to a suitable computing device (e.g., computing device 216 and/or image reconstructor 230) where an image may be reconstructed from the projection data.

At 304, method 300 includes determining gantry imbalance based on output from one or more balance sensors of the CT system (e.g., balance sensor 110 and/or balance sensor 120 of FIG. 1). For example, output from the balance sensor(s) may be sampled while the gantry is rotated and the sampled output may be analyzed to determine if gantry imbalance is higher than an imbalance threshold. If the gantry imbalance is higher than the imbalance threshold, gantry imbalance may be indicated (e.g., by displaying a notification on a display coupled to the computing device) to enable an operator to balance the gantry (e.g., by moving, adjusting, adding, or removing gantry weights) prior to performing any additional CT scans.

At 306, method 300 determines if a gantry vibration measurement is indicated. Gantry vibration may be measured after the CT system has been installed at a location, and before the first CT scan is performed. Additionally or alternatively, gantry vibration may be measured after a new component has been installed in the CT system, maintenance has been performed on the CT system, or other event has occurred where CT performance may be changed or effected. Additionally or alternatively, gantry vibration may be measured after a given period of time has elapsed since a previous gantry vibration was measured (e.g., one day, one week, one month, or one year has elapsed) or a given number of CT scans have been performed since a previous gantry vibration was measured (e.g., fifty scans or one hundred scans). Additionally or alternatively, gantry vibration may be measured in response to a user input requesting gantry vibration be measured (e.g., if an operator detects image quality issues.

If gantry vibration measurement is not indicated, method 300 returns to 302 to selectively rotate the gantry during CT imaging and/or to measure gantry imbalance when indicated. If gantry vibration measurement is indicated, method 300 proceeds to 308 to initiate a vibration monitor that measures gantry vibration using output from the one or more balance sensors. Additional details about the vibration monitor are presented below with respect to FIGS. 4A and 4B. Briefly, to measure gantry vibration, each balance sensor signal is evaluated independently by recovering the original signal with higher order harmonics included and finding the maximum peak-to-peak amplitude of each time-based original balance signal. Such a measurement may include the same signals that are used for measuring gantry balance. However, for measuring gantry balance, the first harmonic of each balance sensor is used together as inputs to a two-plane balance algorithm.

Figure 4A:
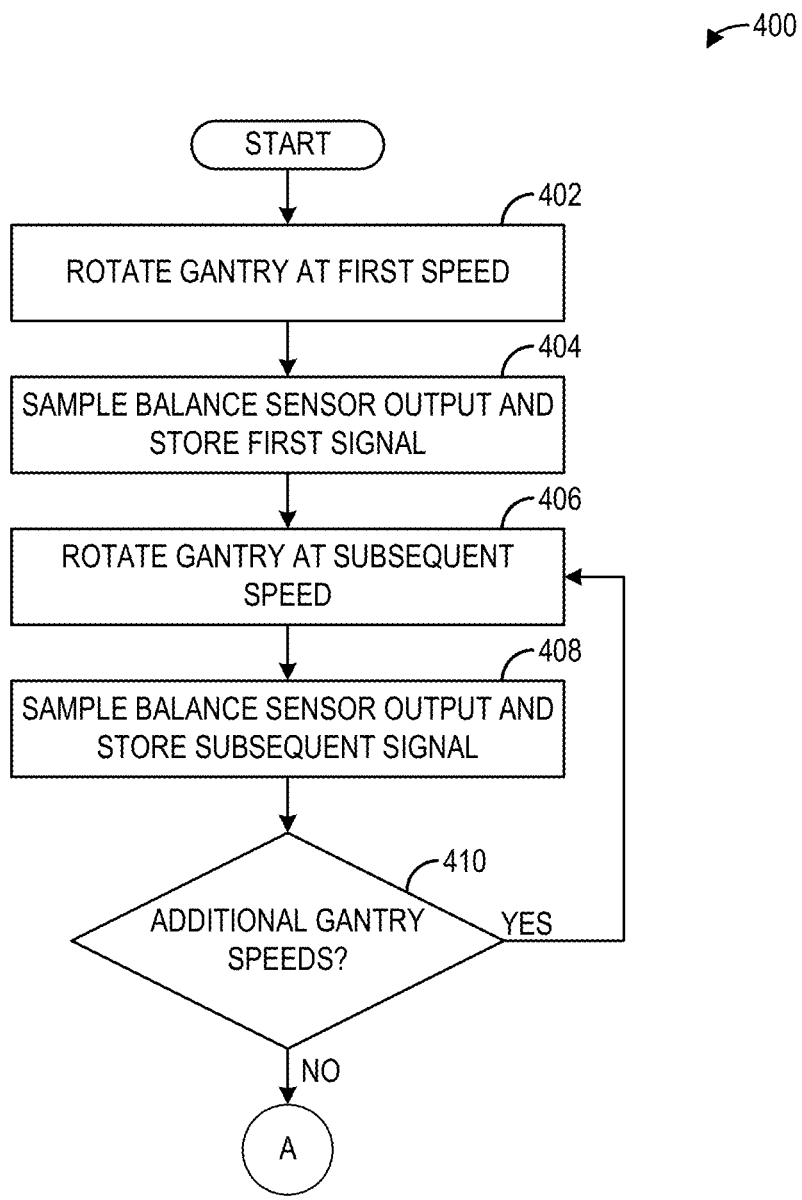
FIGS. 4A and 4B are flow charts illustrating a method for executing a vibration monitor.
Figure 4B:
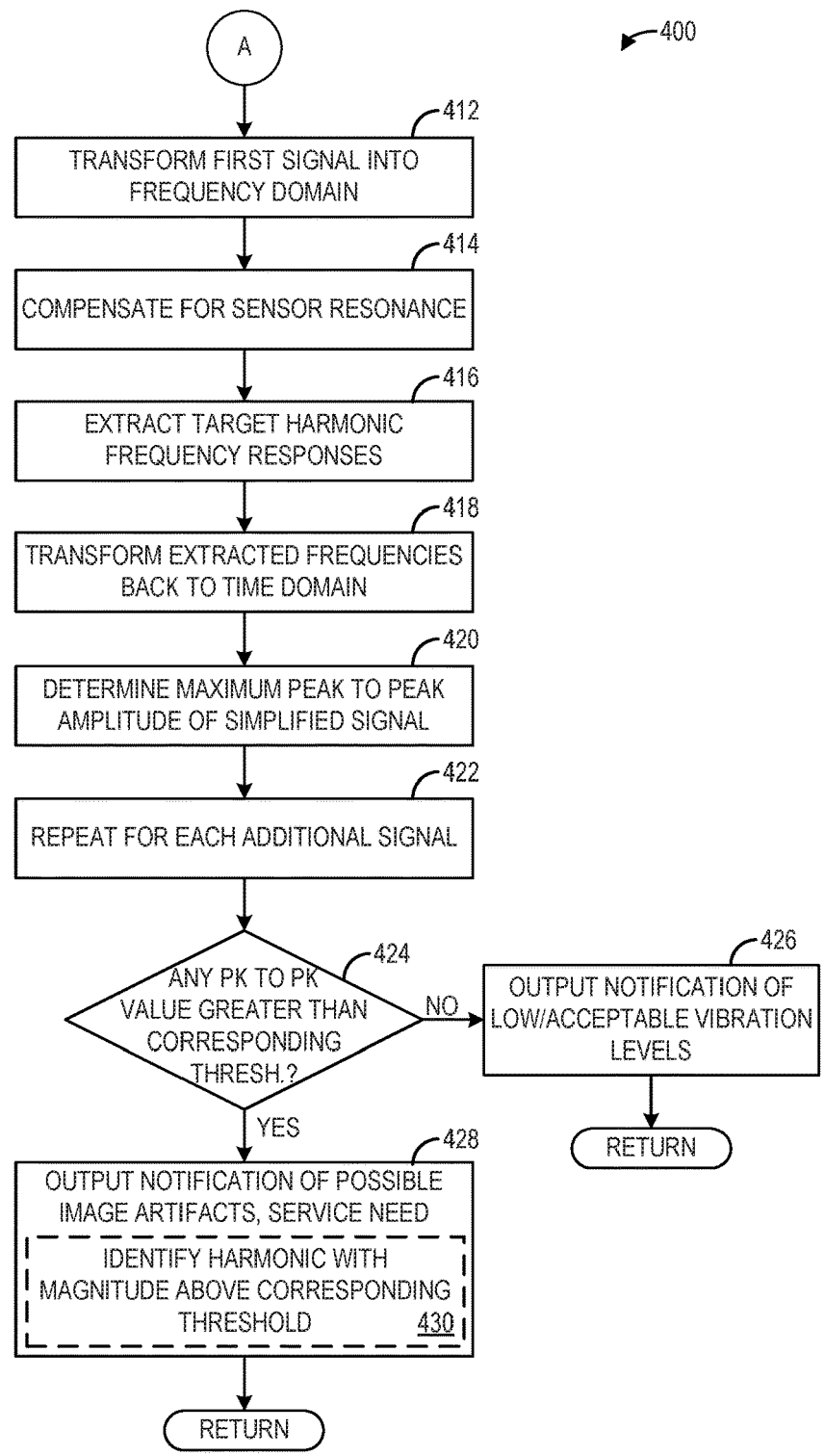

FIGS. 4A and 4B are flow charts illustrating a method 400 for executing a gantry vibration monitor. Method 400 may be executed as part of method 300 described above, in response to an indication to measure gantry vibration. Method 400 may be implemented as executable instructions in non-transitory memory of a computing device, such as computing device 216.

At 402, method 400 includes rotating the gantry at a first speed. The first speed may be a suitable speed, such as one pre-set scanning speed at which the gantry may be operated at during CT image acquisition. In an example, the first speed may be one speed of a set of speeds at which the vibration monitor measures gantry vibrations, and may be the lowest speed at which the gantry vibration monitor is performed. For example, the first speed may be 0.5 Hz (e.g., 30 RPM).

At 404, method 400 includes sampling the balance sensor output and storing the sampled output as a first signal. For example, the output from a balance sensor (such as sensor 110) may be sampled by the computing device and a duration of the output may be saved as a first signal. The duration may be a suitable duration, such as a duration at which 3500 data points may be collected. The balance sensor may output position information indicative of a position of an element of the balance sensor relative to an artificial horizon of the balance sensor (which in some examples may include an angle of the stationary housing), which correlates to movement of the stationary housing on which the balance sensor (and gantry) is coupled.

At 406, method 400 includes rotating the gantry at a subsequent speed. As mentioned above, the gantry may be rotated at a set of speeds during execution of the vibration monitor. After spinning the gantry at the first speed and collecting first balance sensor data, the gantry may be rotated at a second, subsequent speed. The second speed may be higher than the first speed. For example, the first speed may be 0.5 Hz and the second speed may be 1 Hz. At 408, method 400 includes sampling the balance sensor output and storing a subsequent signal from the balance sensor. The subsequent signal may be similar to the first signal, but with the subsequent signal being representative of the stationary housing/balance sensor motion while the gantry is rotated at the corresponding subsequent speed.

At 410, method 400 determines if additional gantry speeds remain in the vibration monitor. For example, the vibration monitor may include ten set gantry speeds, and at 410, method 400 may determine if balance sensor data has been stored for each of the ten speeds. If the vibration monitor includes additional gantry speeds for which balance sensor data has yet to be collected, method 400 returns to 406 to advance the gantry rotation speed to the next subsequent speed (e.g., 1.5 Hz) and collect additional balance sensor data. However, if balance sensor data has been collected for all set gantry speeds, method 400 proceeds to 412, shown on FIG. 4B.

Referring now to method 400 illustrated in FIG. 4B, at 412, method 400 includes transforming the first signal into the frequency domain. As explained above with respect to FIG. 4A, the first signal may include a plurality of balance sensor data points collected over time. At 412, this first signal (collected in the time domain, thus as a function of time) is transformed into the frequency domain using a suitable transformation, such as a discrete Fourier transform. The transformed first signal may be referred to as a sensing complex frequency response. At 414, method 400 includes compensating for a resonance of the balance sensor. The balance sensor measures motion of the stationary housing as a function of the gantry rotation. However, the balance sensor may resonate at certain frequencies, wherein the motion/vibrations of the stationary housing cause the balance sensor to oscillate with greater amplitude at some frequencies than at others. If left uncompensated, the resonance of the balance sensor may result in inaccurate vibration detection of the gantry/stationary housing.

To compensate for the resonance of the balance sensor (also referred to as the characteristics of the balance sensor or dynamic response of the balance sensor), a sensor model may be applied to the transformed first signal/sensing complex frequency response. For example, a transfer function may be determined empirically for the balance sensor and/or CT scanner at the time of manufacture, and the transfer function may be applied to the sensing complex frequency response to remove or correct for the contribution to the measurement signal from the resonance of the balance sensor. Once the contribution from the balance sensor has been corrected for, the remaining signal may be referred to as an original sensing complex frequency response.

At 416, method 400 includes extracting a set of target harmonic frequency responses from the original sensing complex frequency response. The target harmonic frequency responses may represent the frequencies that are most likely to be affected by motion of the gantry. In one example, the set of target harmonic frequency responses may include relatively low frequencies, such as frequencies at or below the sixth order harmonic frequency. CT scanners typically rotate the gantry at relatively low speeds, such as 300 RPM or lower. As such, only the lower harmonics may include useful motion data. In an example, the set of target harmonic frequency responses may include a first order harmonic, a second order harmonic, a third order harmonic, a fourth order harmonic, a fifth order harmonic, and a sixth order harmonic. To extract the target harmonics, a notch filter or other suitable filter may be applied to the original sensing complex frequency response to remove all frequency responses other than the set of target harmonics.

At 418, method 400 includes transforming the extracted frequencies back to the time domain. To transform the extracted frequency responses back to the time domain, a convolution algorithm may be applied, such as an inverse discrete Fourier transform. The transformation results in a simplified vibration signal where all non-informative noise from the signal has been removed. In one example, the simplified vibration signal includes a time-domain signal formed from a sum of only a selected number of sinewaves at each of a selected number of harmonic frequencies, without any other magnitude/frequency components, where the base harmonic frequency is the gantry rotational speed. For example, in one example the base harmonic and only the first 5 higher harmonic frequencies are selected, and thus the simplified time-domain signal is formed from only those six magnitude/frequency pairs. At 420, method 400 includes determining a maximum peak to peak value (e.g., amplitude) of the simplified signal. This maximum peak to peak value may be stored along with the corresponding gantry speed. Further, in some examples, prior to performing the inverse transformation at 418, a magnitude of each target harmonic frequency response may be saved along with the corresponding gantry speed and target harmonic.

At 422, method 400 includes repeating the above process for each additional signal. As explained above, a balance sensor signal may be saved that corresponds to gantry rotation at each speed of the set of gantry speeds, such as the ten gantry speeds. The vibration determination described above (e.g., the transformation into the time domain at 412, compensation for sensor dynamic response at 414, extraction of target harmonics at 416, inverse transformation at 418, and peak to peak determination at 420) may be performed on each stored balance sensor signal.

At 424, method 400 includes determining if any of the determined peak to peak values are greater than a corresponding vibration threshold. As explained above, upon sampling the balance sensor at each gantry speed and then performing the vibration measurement described above on each signal, a peak to peak value for each gantry speed is determined. Each gantry speed may have a corresponding vibration threshold, where a determined peak to peak value that is above that vibration threshold may indicate potential image artifact issues. The vibration threshold for each gantry speed may be determined empirically, for example prior to or at manufacture of the CT scanner, based on an allowable amount of movement of an image subject. For example, a phantom may be placed in the gantry and subject to known levels of vibration, at each gantry speed. An image may be taken of the phantom at each level of vibration and each gantry speed. The lowest level of vibration that results in artifacts or other image quality issues may then be set as the vibration threshold for that gantry speed. The vibration levels may then be saved in memory of the CT scanner computing device.

If none of the peak to peak values are greater than the respective vibration threshold, method 400 proceeds to 426 to output a notification of low and/or acceptable levels of vibration. The notification may include a notification that is displayed on the display device of the CT scanner, for example. The measured vibration levels (e.g., the peak to peak values for each gantry speed) may be displayed in addition or alternative to the notification of the acceptable vibration levels.

If one or more of the peak to peak values are greater than a respective vibration threshold, method 400 proceeds to 428 to output a notification of possible image artifacts and/or a need for CT scanner service. The notification may include a notification that is displayed on the display device of the CT scanner, for example. The measured vibration levels (e.g., the peak to peak values for each gantry speed) may be displayed in addition or alternative to the notification of the possible image artifacts and/or service need. Additionally, in some examples, outputting the notification may include identifying the harmonic(s) with a magnitude above a corresponding threshold, as indicated at 430. For example, if the vibration monitor determined that the CT scanner was exhibiting high vibration at a gantry speed of 1 Hz (e.g., due to the peak to peak value for that balance sensor simplified vibration signal exceeding a vibration threshold), the vibration monitor may then identify which component(s) of the signal (which harmonic frequency response or responses) caused the overall signal to exceed the threshold. To do so, the magnitude of each harmonic frequency response may be compared to a respective threshold. For example, the magnitude of the first order frequency response may be compared to a first threshold, the magnitude of the second order frequency response may be compared to a second threshold, the magnitude of the third order frequency response may be compared to a third threshold, etc. If the magnitude of the third order frequency response is higher than the third threshold, it may indicate a certain type of CT scanner issue that is different than an issue expected to cause the magnitude of the second order frequency response to be higher than the second threshold, for example. Thus, by identifying the affected harmonic, additional information about to service the CT scanner may be provided, thus expediting service.

Thus, a CT scanner may execute a vibration monitor whereby data output from a balance sensor (e.g., inclinometer or other position or velocity sensor) may be analyzed to determine if CT scanner vibrations may cause image quality issues. The vibration monitor determines the motion/vibration amplitude values for each rotation speed of the gantry by sampling data from the on-board balance sensors (while CT system is at constant speed) and deconvolving the digitized sensing signals with the inverse sensing subsystem transfer function in the frequency domain and then extracting the first six harmonic frequency responses, which have been determined to be the most dominant frequencies (for other CT systems, different harmonic ranges may be used).

The original sensing signals are reconstructed, consisting only of the extracted harmonic content. The vibration/motion measurement values are determined as the maximum peak-to-peak amplitude of the reconstructed balance sensing signals. This transfer function (deconvolution algorithm) between vibration/motion and the balance sensors output may be developed for each CT system type and sensor. Depending on the accuracy/repeatability of the sensors and supporting data collection electronics it is possible that this process can be done without calibration on each CT individual scanner produced, but if higher accuracy is desired, calibration offsets can be determined and applied based on an external measurement system (either in the factory before shipping the CT system or replacement sensor) or in the field using an external measurement system. In this way, the motion of the gantry may be monitored during system installation and system upgrades as well as provide a troubleshooting method should image quality issues arise during the lifetime of the CT scanner.

While method 400 described above includes sampling and analysis of a single balance sensor, it should be appreciated that the method may be performed with any number of balance sensors. For example, if a CT scanner includes two balance sensors, data from both the first and second balance sensors may be sampled at each gantry speed and the sampled signals may be analyzed to determine the vibration levels for each sensor. Such an approach may extend the types of vibrations that can be detected, particularly if balance sensors are configured to measure motion in different planes of the CT scanner. In configurations where more than one balance sensor is present and the data from each balance sensor are analyzed to determine the vibration levels, different transfer functions (both the deconvolution and the convolution) may be used for each sensor.

Figure 5:
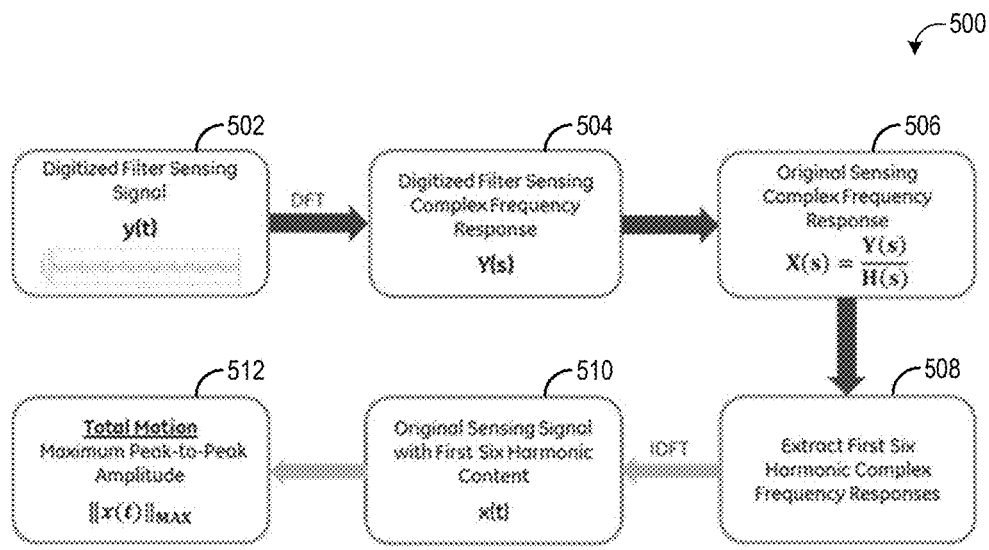
FIG. 5 is a block diagram illustrating a process for a vibration monitor.

FIG. 5 is a block diagram illustrating a process 500 for a vibration monitor. Process 500 may represent the portion of method 400 where the balance sensor signal is analyzed to evaluate vibration relative to an image quality threshold. Block 502 shows the filter sensing signal (termed y(t) in FIG. 5) that is sampled from the balance sensor. A discrete Fourier transform (DFT) is performed on the sensing signal to transform the signal to the frequency domain and generate a filter sensing complex frequency response (referred to as Y(s) in FIG. 5), as shown by block 504. The balance sensor resonance/dynamic response may be compensated for/removed from the frequency response, thus resulting an original sensing complex frequency response at block 506 (which may be represented by X(s), which may be equal to Y(s)/H(s) where H(s) may be the model of the sensor/transfer function). As shown by block 508, the first six harmonic complex frequency responses are extracted from the original sensing complex frequency response and then an inverse DFT is performed to generate an original sensing signal with only the first six harmonic content shown at block 510 (represented as x(t) in FIG. 5 and also referred to herein as the simplified vibration signal). To determine if the vibration levels may impact image quality, the maximum peak to peak amplitude of the signal of block 510 is compared to a limit at 512, where the limit is a function of gantry speed (and is also referred to herein as the vibration threshold).

It is to be understood that the sensing signal may be digitized. In examples where the signal is digitized, the compensation performed at block 506 may include dividing by a model of the system in the Laplace domain. Additionally, low pass filters above the region of interest may be applied to obtain a realizable implementation.

Figure 6:
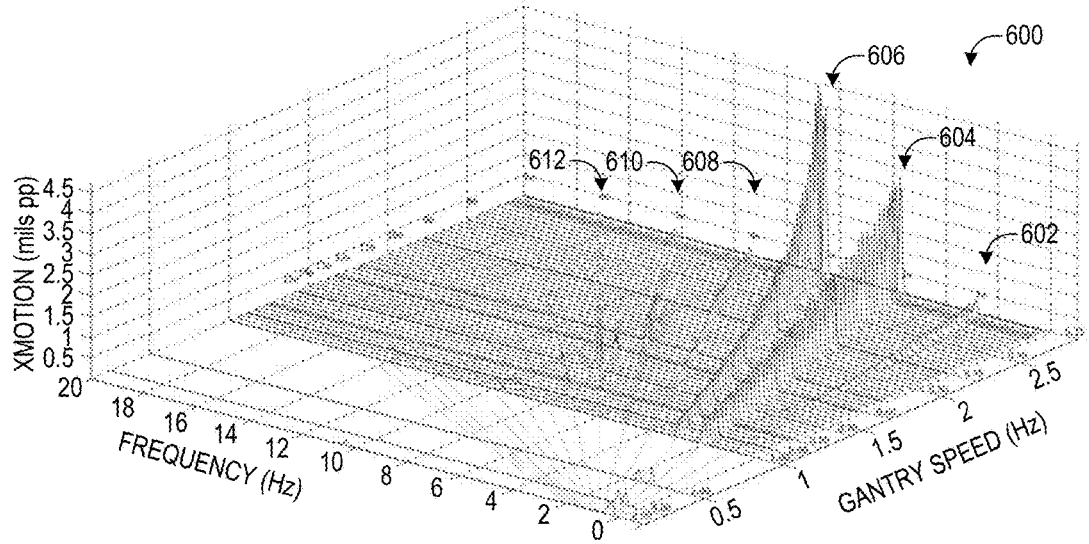
FIG. 6 is graph illustrating example parameters during execution of a vibration monitor.

FIG. 6 is a graph 600 showing gantry motion as a function of gantry speed and signal frequency. Gantry motion (displacement) is plotted along the y-axis and is represented in units of mils peak to peak (pp), where one mil is equal to 0.001 inches. Signal frequency (in Hz) is plotted along the x-axis and gantry speed (also in Hz) is plotted along the z-axis. Example output from the balance sensor, at different frequencies, and at a plurality of different gantry speeds is shown in graph 600. The peak to peak amplitude for each of the first six harmonics at each gantry speed are shown by plots 602-612.

Plot 602 shows sensor output (in the form of peak to peak amplitude) for a first order harmonic (e.g., a frequency of 1 Hz) of the balance sensor signal for a plurality of gantry speeds (e.g., 0.5-2.5 Hz). Plot 604 shows sensor output (in the form of peak to peak amplitude) for a second order harmonic (e.g., a frequency of 2 Hz) of the balance sensor signal for a plurality of gantry speeds (e.g., 0.5-2.5 Hz). Plot 606 shows sensor output (in the form of peak to peak amplitude) for a third order harmonic (e.g., a frequency of 3 Hz) of the balance sensor signal for a plurality of gantry speeds (e.g., 0.5-2.5 Hz). Plot 608 shows sensor output (in the form of peak to peak amplitude) for a fourth order harmonic (e.g., a frequency of 4 Hz) of the balance sensor signal for a plurality of gantry speeds (e.g., 0.5-2.5 Hz). Plot 610 shows sensor output (in the form of peak to peak amplitude) for a fifth order harmonic (e.g., a frequency of 5 Hz) of the balance sensor signal for a plurality of gantry speeds (e.g., 0.5-2.5 Hz). Plot 612 shows sensor output (in the form of peak to peak amplitude) for a sixth order harmonic (e.g., a frequency of 6 Hz) of the balance sensor signal for a plurality of gantry speeds (e.g., 0.5-2.5 Hz).

The first order harmonic (shown by plot 602) is the vibration from imbalance and is what is measured when balancing a system to reduce the vertical amplitude to as close to 0 as possible. As can be appreciated from FIG. 6, there are other harmonics contributing to the vibration of the system that are not first order, but are instead second order, third order, and higher. These harmonics are due to other disturbances in the gantry. For example, second order (something that occurs twice per revolution, shown by plot 604) may be related to the CT scanner having a very heavy X-ray tube which is 180 degrees opposite the heavy CT detector. These two components pull on the gantry bearing, in opposite directions, while the gantry is rotating and cause distortion which results in vibration. Further, the third order harmonic (shown by plot 606) also exhibits a high degree of motion. For each signal frequency, motion increases with increasing gantry speed.

When a gantry is balanced, the motion shown by the first order frequency is adjusted, but not the other orders which may result from the gantry design as well as other factors such as the building stiffness, stiffness of the floor supporting the gantry, etc. The total vibration of the CT scanner is the summation of all captured harmonics (with their corresponding phase shifts). Because of this, the balance data alone (plot 602) is not enough to determine the vibration/motion of a gantry, and thus the embodiments disclosed herein sum together the first six harmonics to use the full data available from the balance sensors (not just the imbalance data) and combines it with a deconvolution algorithm approach (as depicted in FIG. 5) to determine to total vibration/motion of the CT scanner. All of this is accomplished without the need for any new or externally attached hardware.

A technical effect of measuring CT scanner rotation using output from a balance sensor is detection of CT scanner vibration that may cause image quality issues without relying on additional sensors or external hardware.

An example provides a method for a computed tomography (CT) system including measuring a vibration level of a rotatable gantry of the CT system with a balance sensor coupled to a stationary housing of the CT system; and outputting a notification indicating potential image artifacts based on the vibration level exceeding a vibration threshold. In a first example of the method, measuring the vibration level with the balance sensor comprises measuring the vibration level with one or more of an inclinometer, accelerometer, or velocity sensor. In a second example of the method, which optionally includes the first example, measuring the vibration level comprises measuring a first vibration level at a first gantry speed, and the method further includes measuring a plurality of additional vibration levels at respective, different gantry speeds, and outputting the notification indicating potential image artifacts based on any one of the plurality of additional vibration levels exceeding a corresponding vibration threshold. In a third example of the method, which optionally includes one or both of the first and second examples, measuring the vibration level with the balance sensor comprises: sampling output of the balance sensor to generate a balance sensor signal in the time domain; transforming the sensor balance signal into the frequency domain to generate a complex frequency response; extracting a set of target harmonic frequency responses from the complex frequency response; and transforming the set of target harmonic frequency responses back to the time domain to generate a simplified vibration signal, where the vibration level is a peak to peak value measured from the simplified vibration signal. In a fourth example of the method, which optionally includes one or more or each of the first through third examples, the balance sensor includes an internal resonance, and the method further includes removing a contribution to the complex frequency response from the internal resonance prior to extracting the set of target harmonic frequency responses. In a fifth example of the method, which optionally includes one or more or each of the first through fourth examples, the set of target harmonic frequency responses comprises a first order harmonic frequency response, a second order harmonic frequency response, a third order harmonic frequency response, a fourth order harmonic frequency response, a fifth order harmonic frequency response, and a sixth order harmonic frequency response. In a sixth example of the method, which optionally includes one or more or each of the first through fifth examples, the method further includes, responsive to the vibration level exceeding the vibration threshold, identifying one or more target harmonic frequency responses of the set of target harmonic frequency responses that is greater than a corresponding frequency response threshold and outputting a notification of the identified one or more target harmonic frequency responses.

An example provides a computed tomography system including a stationary housing; a rotatable gantry housed in the stationary housing, a radiation source and radiation detector coupled on opposite sides of the gantry; a balance sensor coupled to the stationary housing; and a controller. The controller stores instructions executable to: rotate the gantry at a first speed; sample output from the balance sensor while the gantry is rotating at the first speed and transform the output to the frequency domain; correct the transformed output to remove a contribution from a resonance of the balance sensor to the transformed output; determine, from the corrected transformed output, a vibration level of the rotatable gantry while rotating at the first speed; and output a notification indicating potential image artifacts based on the vibration level exceeding a vibration threshold. In a first example of the system, the instructions are executable to, based on the vibration level not exceeding the vibration threshold, selectively rotate the rotatable gantry and activate the radiation source to acquire projection data from the radiation detector of a subject positioned within the rotatable gantry, the projection data usable to reconstruct an image of the subject. In a second example of the system, which optionally includes the first example, the instructions are executable to apply a convolution model to the transformed output to correct the transformed output. In a third example of the system, which optionally includes one or both of the first and second examples, the instructions are executable to extract a set of target harmonic frequency responses from the corrected transformed output, apply a deconvolution model to the extracted set of target harmonic frequency responses to generate a simplified vibration signal in the time domain, and determine the vibration level by measuring a peak to peak value of the simplified vibration signal. In a fourth example of the system, which optionally includes one or more or each of the first through third examples, the instructions are executable to measure imbalance of the gantry based on output from the balance sensor. In a fifth example of the system, which optionally includes one or more or each of the first through fourth examples, the vibration level is a first vibration level, and the instructions are executable to: rotate the gantry at a second speed; determine a second vibration level of the rotatable gantry while rotating at the second speed; and output a notification indicating potential image artifacts based on the second vibration level exceeding a second vibration threshold that is different than the first vibration threshold. In a sixth example of the system, which optionally includes one or more or each of the first through fifth examples, the balance sensor is an inclinometer. In a seventh example of the system, which optionally includes one or more or each of the first through sixth examples, the balance sensor is a first balance sensor configured to measure vibration along a first plane of the CT system, and the system further includes a second balance sensor configured to measure vibration along a second plane of the CT system, orthogonal to the first plane.

An example provides a method for a computed tomography (CT) system including rotating a gantry of the CT system at a first speed; measuring a vibration level of the CT system while the gantry is rotating at the first speed, the measuring including: sampling output from a balance sensor of the CT system while the gantry is rotating at the first speed to generate a sensor vibration signal; compensating for dynamics of the balance sensor and simplifying the sensor vibration signal by transforming the sensor vibration to the frequency domain, applying a sensor model to the transformed output, removing higher order harmonic frequency responses, and transforming the remaining, lower order harmonic frequency responses back to the time domain as a single, simplified vibration signal; and determining a peak to peak value of the simplified vibration signal, where the vibration level is the peak to peak value; and outputting a notification indicating potential image artifacts based on the vibration level exceeding a vibration threshold. In a first example of the method, removing the higher order harmonic frequency responses comprises removing all harmonic frequency responses other than a first order, a second order, a third order, a fourth order, a fifth order, and a sixth order harmonic frequency response. In a second example of the method, which optionally includes the first example, the method further includes measuring gantry imbalance based on output from the balance sensor. In a third example of the method, which optionally includes one or both of the first and second examples, sampling output from the balance sensor comprises sampling output from an inclinometer coupled to a stationary housing of the CT system configured to house the gantry.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a computed tomography (CT) system, comprising:
    measuring a vibration level of a rotatable gantry of the CT system with a balance sensor coupled to a stationary housing of the CT system, the vibration level including a peak to peak value measured from a simplified vibration signal, the simplified vibration signal based on a set of target harmonic frequency responses extracted from output from the balance sensor; and
    outputting a notification indicating potential image artifacts based on the vibration level exceeding a vibration threshold.

2. The method of claim 1, wherein measuring the vibration level with the balance sensor comprises measuring the vibration level with one or more of an inclinometer, an accelerometer, or a velocity sensor.

3. The method of claim 1, wherein measuring the vibration level comprises measuring a first vibration level at a first gantry speed, and further comprising measuring a plurality of additional vibration levels at respective, different gantry speeds, and outputting the notification indicating potential image artifacts based on any one of the plurality of additional vibration levels exceeding a corresponding vibration threshold.

4. The method of claim 1, wherein measuring the vibration level with the balance sensor comprises:
    sampling the output of the balance sensor to generate a balance sensor signal in a time domain;
    transforming the sensor balance signal into a frequency domain to generate a complex frequency response;
    extracting the set of target harmonic frequency responses from the complex frequency response; and
    transforming the set of target harmonic frequency responses back to the time domain to generate the simplified vibration signal.

5. The method of claim 4, wherein the balance sensor includes an internal resonance, and further comprising removing a contribution to the complex frequency response from the internal resonance prior to extracting the set of target harmonic frequency responses.

6. The method of claim 4, wherein the set of target harmonic frequency responses comprises a first order harmonic frequency response, a second order harmonic frequency response, a third order harmonic frequency response, a fourth order harmonic frequency response, a fifth order harmonic frequency response, and a sixth order harmonic frequency response.

7. The method of claim 4, further comprising, responsive to the vibration level exceeding the vibration threshold, identifying one or more target harmonic frequency responses of the set of target harmonic frequency responses that is greater than a corresponding frequency response threshold and outputting a notification of the identified one or more target harmonic frequency responses.

8. A computed tomography (CT) system, comprising:
    a stationary housing;
    a rotatable gantry housed in the stationary housing, and a radiation source and a radiation detector coupled on opposite sides of the gantry;
    a balance sensor coupled to the stationary housing; and
    a controller storing instructions executable to:
        rotate the gantry at a first speed;
        sample output from the balance sensor while the gantry is rotating at the first speed and transform the output to a frequency domain;
        correct the transformed output to remove a contribution from a resonance of the balance sensor to the transformed output;
        determine, from the corrected transformed output, a vibration level of the gantry while rotating at the first speed; and
        output a notification indicating potential image artifacts based on the vibration level exceeding a vibration threshold.

9. The system of claim 8, wherein the instructions are executable to, based on the vibration level not exceeding the vibration threshold, selectively rotate the gantry and activate the radiation source to acquire projection data from the radiation detector of a subject positioned within the gantry, the projection data usable to reconstruct an image of the subject.

10. The system of claim 8, wherein the instructions are executable to apply a convolution model to the transformed output to correct the transformed output.

11. The system of claim 10, wherein the instructions are executable to extract a set of target harmonic frequency responses from the corrected transformed output, apply a deconvolution model to the extracted set of target harmonic frequency responses to generate a simplified vibration signal in a time domain, and determine the vibration level by measuring a peak to peak value of the simplified vibration signal.

12. The system of claim 8, wherein the instructions are executable to measure an imbalance of the gantry based on the output from the balance sensor.

13. The system of claim 8, wherein the vibration level is a first vibration level, and wherein the instructions are executable to:
rotate the gantry at a second speed;
determine a second vibration level of the gantry while rotating at the second speed; and
output a notification indicating potential image artifacts based on the second vibration level exceeding a second vibration threshold that is different than the first vibration threshold.

14. The system of claim 8, wherein the balance sensor is an inclinometer.

15. The system of claim 8, wherein the balance sensor is a first balance sensor configured to measure vibration along a first plane of the CT system, and further comprising a second balance sensor configured to measure vibration along a second plane of the CT system, orthogonal to the first plane.

16. A method for a computed tomography (CT) system, comprising:
rotating a gantry of the CT system at a first speed;
measuring a vibration level of the CT system while the gantry is rotating at the first speed, the measuring including:
sampling output from a balance sensor of the CT system while the gantry is rotating at the first speed to generate a sensor vibration signal;
compensating for dynamics of the balance sensor and simplifying the sensor vibration signal by transforming the sensor vibration signal to a frequency domain, applying a sensor model to the transformed output, removing higher order harmonic frequency responses, and transforming remaining, lower order harmonic frequency responses back to a time domain as a single, simplified vibration signal; and
determining a peak to peak value of the simplified vibration signal, where the vibration level is the peak to peak value; and
outputting a notification indicating potential image artifacts based on the vibration level exceeding a vibration threshold.

17. The method of claim 16, wherein removing the higher order harmonic frequency responses comprises removing all harmonic frequency responses other than a first order, a second order, a third order, a fourth order, a fifth order, and a sixth order harmonic frequency response.

18. The method of claim 16, further comprising measuring a gantry imbalance based on the output from the balance sensor.

19. The method of claim 16, wherein sampling the output from the balance sensor comprises sampling output from an inclinometer coupled to a stationary housing of the CT system configured to house the gantry.

* * * * *